United States Patent [19]

Lam

[11] Patent Number: 4,487,706

[45] Date of Patent: Dec. 11, 1984

[54] METAL DEACTIVATOR AS A LUBRICANT ADDITIVE

[75] Inventor: William Y. Lam, St. Louis, Mo.

[73] Assignee: Edwin Cooper, Inc., St. Louis, Mo.

[21] Appl. No.: 466,529

[22] Filed: Feb. 15, 1983

[51] Int. Cl.$^3$ .............................................. C10M 1/38
[52] U.S. Cl. .................................... 252/47; 252/47.5; 548/142
[58] Field of Search .................. 252/47, 47.5; 548/142

[56] References Cited

U.S. PATENT DOCUMENTS

| 2,719,125 | 9/1955 | Roberts | 252/46.7 |
| 3,087,932 | 4/1963 | Little, Jr. | 260/302 |
| 3,663,561 | 5/1972 | Blaha | 260/302 |
| 3,821,236 | 6/1974 | Ripple | 252/47 |
| 3,840,549 | 10/1974 | Blaha et al. | 252/47 |
| 4,097,387 | 6/1978 | Caspari | 252/47.5 |

OTHER PUBLICATIONS

E. K. Fields, "Industrial and Engineering Chemistry" 49 pages, 1361–1364 (Sep. 1957).

Primary Examiner—Jacqueline V. Howard
Attorney, Agent, or Firm—Donald L. Johnson; John F. Sieberth; W. G. Montgomery

[57] ABSTRACT

A metal deactivator especially useful in lubricating oil is made by reacting 2,5-dimercapto-1,3,4-thiadiazole, an olefin and sulfur dichloride in the mole ratio of about 1:0.9–2.5 0.9–2.5.

18 Claims, No Drawings

METAL DEACTIVATOR AS A LUBRICANT ADDITIVE

BACKGROUND

Metal deactivators have been used for many years to inhibit metal corrosion. They are especially useful in lubricating oils to prevent sulfur induced corrosion of copper and copper alloys such as copper-lead bearings. One useful additive of this type is described in U.S. Pat. No. 2,719,125 wherein 1,3,4-thiadiazole 2,5-bis(alkyldisulfides) are made by reacting 2,5-dimercapto-1,3-4-thiadiazole (DMTD) with sulfenyl chloride or chlorine to form a di-sulfenylchloride intermediate which is reacted with a primary or tertiary mercaptan. Alternatively, the additives can be made by reacting DMTD with mercaptan and sulfur in a 1:1:1 molar ratio.

The preparation of various derivatives of DMTD is described in E. K. Fields "Industrial and Engineering Chemistry" 49 p. 1361–4 (Sept. 1957).

A method of making 2,5-bis(alkyldithio)-1,3,4-thiadiazole is disclosed in U.S. Pat. No. 3,087,932. This process involves the reaction of hydrogen peroxide with a mixture of DMTD or its alkali metal salt and an alkyl mercaptan.

U.S. Pat. No. 3,663,561 describes 2-hydrocarbyl-dithio-1,3,4-thiadiazoles which are useful as metal deactivators. They are made by reacting equimole amounts of a hydrocarbyl mercaptan and DMTD or its alkali metal salt in the presence of an oxidizing agent such as a peroxide, a hypohalite or oxygen.

More recently, U.S. Pat. No. 4,097,387 describes DMTD derived metal deactivators made by reacting a sulfur halide with an olefin to form an intermediate which is reacted with an alkali metal salt of DMTD.

SUMMARY

According to the present invention highly effective metal passivators provided by reacting an olefin, sulfur dichloride and DMTD preferably in one reaction.

DESCRIPTION OF THE PREFERRED EMBODIMENTS

A preferred embodiment of the invention is a product made by process comprising reacting (a) about one mole of 2,5-dimercapto-1,3,4-thiadiazole, (b) about 0.9–2.5 moles of an olefin containing 6–30 carbon atoms and (c) about 0.9–2.5 moles of sulfur dichloride at a temperature of about 30° C. to reflux.

Many olefins can be used to make the present additive. These include n-hexene-1, 2-ethyl hexene-1, n-octene-1, 2,2,4-trimethyl pentene-1, 2-ethyl decene-1, dodecene-1, tetradecene-1, 2-ethyl tetradecene-1, octadecene-1, ercosene-1, 2-propyl erosene-1, tetracosene-1, triacontene-1 and the like.

A preferred class of olefins consists of the oligomers of the lower olefins such as propylene, isobutylene and the like including mixtures thereof and the like. Examples of these are propylene trimer, propylene tetramer, isobutylene dimer, isobutylene trimer and mixtures thereof. The most preferred olefin is diisobutylene consisting mainly of 2,2,4-trimethyl pentene-1.

An operable ratio of DMTD:olefin:sulfur dichloride is 1:0.9–2.5:0.9–2.5. A more preferred mole ratio is 1:1.9–2.2:1.9–2.2. The most preferred mole ratio is about 1:2:2.

Although not essential, it is preferred that the process be conducted in an inert solvent. These include aliphatic and aromatic hydrocarbons such as heptane, octane, petroleum ether, benzene, toluene, xylene and the like. Preferred solvents comprise the halogenation hydrocarbons such as methylene chloride, chloroform, carbon tetrachloride, 1,2-dichloroethane, 1,1-dichloroethane, 1,1,2-trichloroethane, chlorobenzene, dichlorobenzene and the like.

In a highly preferred embodiment the solvent has a normal or atmospheric boiling point below 200° C. more preferably below 100° C. Such solvents can function to limit the maximum temperature of the reaction to reflux temperature. For example, methylene chloride, (i.e. dichloromethane) (b.p. 40° C.), chloroform (b.p. 61° C.) 1,1-dichloroethane (b.p. 57° C.) 1,2-dichloroethane (b.p. 83.5° C.) and 1,1,2-trichloroethane can be used to control maximum temperature.

The process can be conducted by merely mixing all three reactants and heating the mixture. In a more preferred embodiment the olefin and DMTD are mixed including a solvent if used and the sulfur dichloride added slowly to the stirred mixture. The reaction temperature can initially be at ambient temperature but is preferabe raised to 30° C. to reflux during the course of the reaction. A more preferred reaction temperature is about 50°–100° C. or reflux.

The initial product is believed to have the structure:

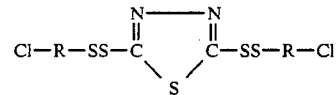

wherein R is an aliphatic hydrocarbon group containing about 6–30 carbon atoms.

Some HCl evolves during the course of the reaction introducing olefinic unsaturation into the aliphatic hydrocarbon group. The final product can be shown as

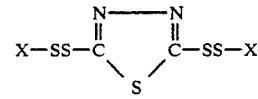

wherein X is selected from —R—Cl and an olefinically unsaturated aliphatic hydrocarbon group. The product is a mixture in which both types of X are present which makes it easier and more accurate to define the product by the process used in its preparation.

The reaction is conducted for a time sufficient to form an effective product. A longer time is required at lower temperature. At 70° C. the reaction is complete in about 2.5 hours. Accordingly, a useful reaction time can vary from about 1–4 hours depending on temperature.

The product is worked up by conventional means. Good results have been achieved when using a halogenated hydrocarbon solvent by washing with water and drying over anhydrous sodium sulfate. The solvent is then distilled out preferably under vacuum to obtain an oily product. Any solids can be removed by filtration.

The following examples serve to illustrate how the process can be carried out.

EXAMPLE 1

In a reaction vessel was placed 50 g chloroform, 27 g (0.24 m) diisobutylene and 15 g (0.1 m) DMTD. This mixture wasstirred under nitrogen and 20.6 g (0.2 m)

sulfur dichloride was added dropwise. The temperature was increased to 40°-45° C. and HCl evolved. After sulfur dichloride addition was complete the mixture was heated to reflux (71° C.) and held at this temperature for 2.5 hours. The resultant product was washed with aqueous brine and dried over anhydrous sodium sulfate. Solvent was distilled out under vacuum up to 100° C. leaving a dark brown oily product. The product was filtered. It analyzed 36.2 weight percent sulfur and 5.8 weight percent chlorine.

EXAMPLE 2

In a reaction vessel was placed 200 ml toluene, 67.2 g (0.6 mol) diisobutylene and 45 g (0.3 mol) DMTD. While stirring 61.8 g (0.6 mol) sulfur dichloride was added dropwise at 50° C. Hydrogen chloride evolved throughout the addition. Addition was complete in about 45 minutes and the mixture was then stirred at 80°-90° C. for 2 hours. The mixture was filtered and the filtrate washed with water. The filtrate was again filtered. The aqueous layer was removed and the organic layer washed with dilute aqueous caustic and then twice with water. Toluene was distilled under vacuum leaving an oily product analyzing 41.3 weight percent S and 5.50 weight percent Cl.

EXAMPLE 3

In a reaction vessel was placed 150 g. chloroform, 44.8 g (0.4 mol) diisobutylene and 30 g (0.2 mol) DMTD. While stirring 41.2 g (0.4 mol) of sulfur dichloride was added dropwise at 50° C. Hydrogen chloride evolved during the addition. The mixture was then heated to reflux (approximately 70° C.) and held there for 2 hours. The product was washed with water and filtered. The filtrate was again washed with water and filtered. The filtrate was again water washed and then the solvent was distilled out at 100° C. under vacuum leaving a viscious brown liquid product.

The products are useful in a wide range of lubricating oils such as crankcase oil for gasoline or diesel engines. It is effective in gear oil formulation and automatic transmission fluids. It can also be used in functional fluids such as hydraulic fluids.

The lubricating oil can be a mineral oil, a synthetic oil or a blend of both. Useful mineral oils include solvent refined oil, hydrotreated oil and the like. Synthetic oils include olefin oligomer especially $C_{6-12}$ oligomer containing an average of about 26–50 carbon atoms per molecule. An especially useful olefin oligomer is a mixture of mainly α-decene trimer and tetramer.

Likewise, alkylaromatics can be used as the base lubricating oil such as octadecylbenzene, didodecylbenzene, dioctadecylbenzene and the like including mixtures thereof.

Synthetic ester lubricants are also useful such as dinonyl adipate, trimethylolpropane tripelargonate and the like.

The lubricating oil can also contain other conventional additives such as a sulfurized isobutylene wear inhibitor, antioxidant such as zinc dialkyldithiophosphate, viscosity index improvers, phosphate esters or acid phosphate esters.

The present additive is an effective metal corrosion inhibitor at very low concentrations. The amount needed depends upon the amounts of active sulfur in the lubricating oil. A useful range is about 0.05–10 weight percent. A more preferred concentration is 1.0–7.0 weight percent. In gear oil formulations containing a sulfurized wear inhibitor such as sulfurized isobutylene good results have been obtained at 2–6 weight percent.

Tests were conducted which demonstrate the effectiveness of the present products in preventing copper corrosion. The first test is the Copper Corrosion Test (CCT). This test is carried out as follows:

A clean polished, weighed copper strip, approximately ½"×3"×1/16" is immersed in 30 g of sulfurized isobutylene, a commercial wear inhibitor known to be corrosive to copper, at 121° C. for 3 hours. The strip is then rinsed with solvent, wiped clean of loose corrosion, and immersed in 10% KNC solution for 5 minutes. The KCN treated strip is washed with water, dried with acetone, and then weighed.

The test samples used no mineral oil, only neat sulfurized isobutylene containing the inhibitor was used. Test criteria is the mg of weight loss due to corrosion during the test.

Results were as follows:

| Additive | Conc. (wt. %) | Wt. Loss (mg) |
| --- | --- | --- |
| None | — | 131 |
| From Example 1 | 0.2 | 63 |

Another test conducted was the ASTM D-130 Test which measures the copper staining properties of an oil containing a sulfurized wear inhibitor. The test oil was a neutral mineral oil containing 2 or 5.25 weight percent of a commercial gear oil package which contained a sulfurized isobutylene wear inhibitor and 2.0 weight percent of the test additive. A clean polished copper strip is immersed in the test oil at 121° C. for 3 hours and then rated visually on a scale from 1a (clean and bright) to 4c (black) using ASTM standard strips for comparison.

Results of the tests were as follows:

| | ASTM RATING Gear Oil Pkg Conc | |
| --- | --- | --- |
| Additive | 2.0 wt % | 5.25 wt % |
| none | 3b | 3b |
| Example 1 | 1b | 1b |
| Example 2 | 1b | 1b |
| Example 3 | 1b | 1b |

These results show that the present additives control copper corrosion and inhibit tarnish of copper surfaces.

I claim:

1. A metal deactivator made by a process comprising reacting (a) about one mole of 2,5-dimercapto-1,3,4-thiadiazole, (b) about 0.9–2.5 moles of an olefin containing 6–30 carbon atoms and (c) about 0.9–2.5 moles of sulfur dichloride at a temperature of about 30° C. to reflux.

2. A metal deactivator of claim 1 wherein the amount of olefin is about 1.8–2.5 moles and the amount of sulfur dichloride is about 1.8–2.5 moles.

3. A metal deactivator of claim 2 prepared in a chlorohydrocarbon solvent having a normal boiling point below 200° C.

4. A metal deactivator of claim 2 wherein said olefin is diisobutylene.

5. A metal deactivator of claim 4 wherein the amount of diisobutylene is about 1.9–2.2 moles.

6. A metal deactivator of claim 5, wherein the amount of sulfur dichloride is about 1.9–2.2 moles.

7. A process for making a metal deactivator, said process comprising reacting (a) about one mole of 2,5-dimercapto-1,3,4-thiadiazole (b) about 0.9–2.5 moles of an olefin containing 6–30 carbon atoms and (c) about 0.9–2.5 moles of sulfur dichloride at a temperature of about 30° C. to reflux.

8. A process of claim 7 wherein the amount of olefin is about 1.8–2.5 moles and the amount of sulfur dichloride is about 1.8–2.5 moles.

9. A process of claim 8 prepared in a chlorohydrocarbon solvent having a normal boiling point below 200° C.

10. A process of claim 7 wherein said olefin is diisobutylene.

11. A process of claim 10 wherein the amount of diisobutylene is about 1.9–2.2 moles.

12. A process of claim 11 wherein the amount of sulfur dichloride is about 1.9–2.2 moles.

13. A lubricating oil composition containing a metal deactivating amount of a product made by a process comprising reacting (a) about one mole of 2,5-dimercapto-1,3,4-thiadiazole (b) about 0.9–2.5 moles of an olefin containing 6–30 carbon atoms and (c) about 0.9–2.5 moles of sulfur dichloride at a temperature of about 30° C. to reflux.

14. A lubricating oil composition of claim 13 wherein the amount of olefin is about 1.8–2.5 moles and the amount of sulfur dichloride is about 1.8–2.5 moles.

15. A lubricating oil composition of claim 14 prepared in a chlorohydrocarbon solvent having a normal boiling point below 200° C.

16. A lubricating oil composition of claim 14 wherein said olefin is diisobutylene.

17. A lubricating oil composition of claim 16 wherein the amount of diisobutylene is about 1.9–2.2 moles.

18. A lubricating oil composition of claim 17 wherein the amount of sulfur dichloride is about 1.9–2.2 moles.

* * * * *